United States Patent [19]

Southern

[11] 4,100,923
[45] Jul. 18, 1978

[54] EXTRA-AMNIOTIC ADMINISTRATION DEVICE

[75] Inventor: Edward M. Southern, Kalamazoo, Mich.

[73] Assignee: The Upjohn Company, Kalamazoo, Mich.

[21] Appl. No.: 751,096

[22] Filed: Dec. 16, 1976

[51] Int. Cl.² ............................................ A61M 25/00
[52] U.S. Cl. .................................... 128/348; 128/129; 128/246; 128/344; 128/349 B
[58] Field of Search ................................ 128/348–351, 128/343, 344, 325, 246, 130, 131, 129

[56] References Cited

U.S. PATENT DOCUMENTS

| 2,230,150 | 1/1941 | Winder | 128/349 B |
| 2,553,428 | 5/1951 | Sokolik | 128/131 |
| 3,848,602 | 11/1974 | Gutnick | 128/344 |

FOREIGN PATENT DOCUMENTS

| 334,404 | 1/1936 | Italy | 128/344 |

Primary Examiner—Dalton L. Truluck
Attorney, Agent, or Firm—Blanchard, Flynn, Thiel, Boutell & Tanis

[57] ABSTRACT

The extra-amniotic device has an elongated, flexible tube capable of insertion through the cervix and into the extra-amniotic space of an impregnated uterus. A pair of resiliently flexible flanges are secured to said tube and spaced from each other so that the inner flange can be located within the uterus adjacent the internal os when the outer flange is located within the birth canal adjacent the external os. A resiliently flexible, substantially cylindrical member surrounds the tube between said flanges and is secured to said tube at the opposite axial ends thereof in an air-tight manner. Said member is connected to conduit means which can extend through part of the cervix and the birth canal for connection to a source of fluid under pressure whereby said member is inflated. The outer end of said tube is connected by conduit means to a source of liquid, which may be a medication.

5 Claims, 2 Drawing Figures

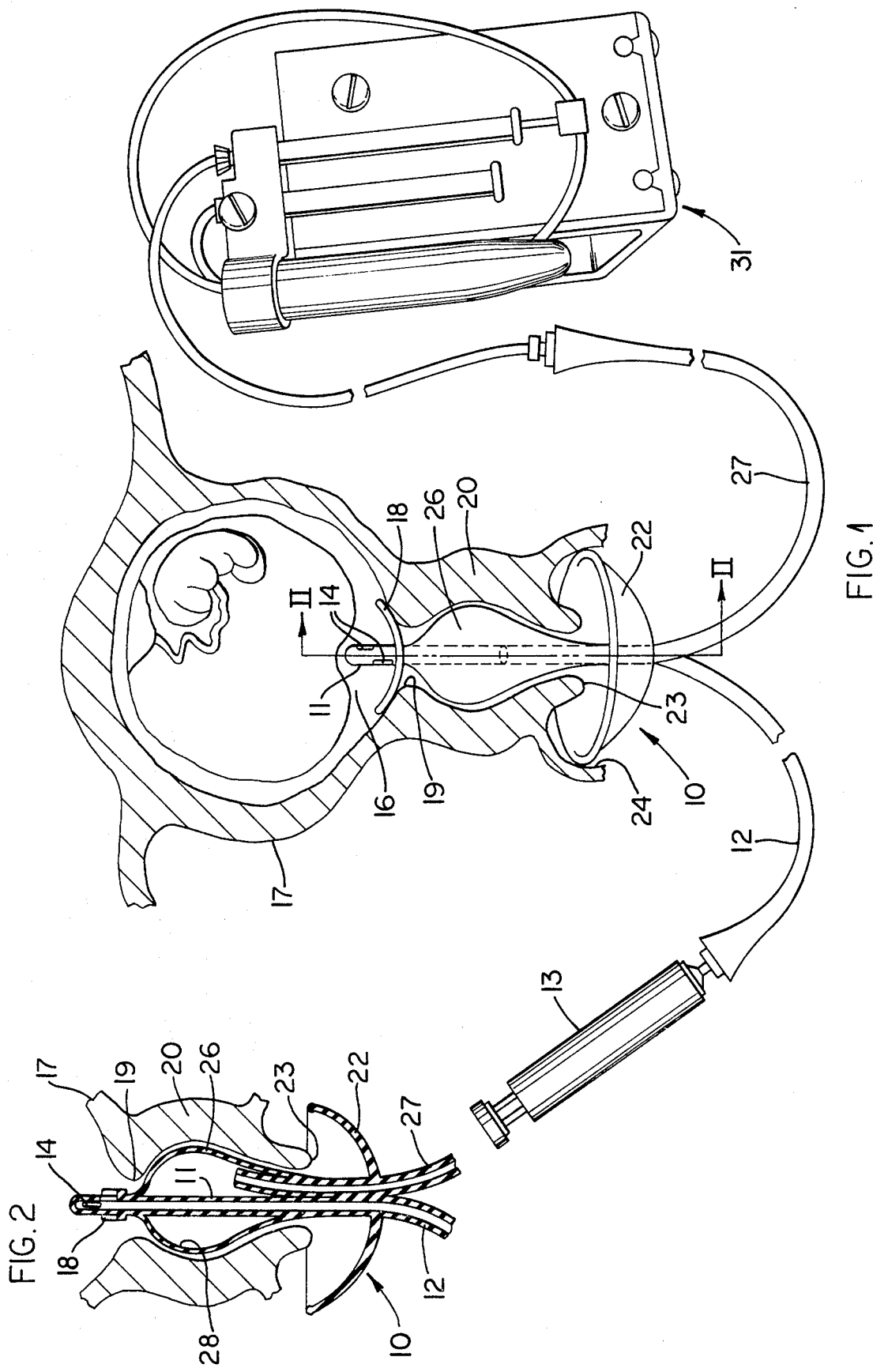

EXTRA-AMNIOTIC ADMINISTRATION DEVICE

BACKGROUND OF THE INVENTION

This invention relates in general to a method and catheter for delivering a liquid into a uterus from an external source and, more particularly, for administering medication to the extra-amniotic space in an impregnated uterus during the first or second trimester whereby the fetus is aborted.

Numerous attempts have been made to provide a catheter capable of safe and easy operation for the purpose of administering liquid medications into an impregnated uterus. Examples of existing such devices are shown in the following patents herewith:

Kistler Pat. No. 868 450; Miller Pat. No. 3 459 176; Bell Pat. No. 3 509 884; and Gutnick Pat. No. 3 848 602.

Other, less relevant patents include: Knapp Pat. No. 397 060; Lamson No. Pat. 2 457 244; and Matthews et al. Pat. No. 3 253 594.

Applicant believes that the invention claimed herein is clearly distinguishable from the aforesaid prior art.

Existing devices have all failed for one reason or another to provide safe, optimum results particularly where the purpose is to abort a fetus in the second trimester. Drugs which have been particularly successful in effecting abortion include, but are not necessarily limited to, the following:

$PGE_2$ or a salt thereof
$PGF_{2\alpha}$ or a salt thereof

These drugs are discussed in U.S. Pat. No. 3 852 465 entitled: ABORTION BY MYOMETRIAL ADMINISTRATION OF PROSTAGLANDINS.

Existing catheters for delivering liquid medication into a uterus have not been formed to fit snugly and properly within the cervix and, accordingly, either the cervix has been unnaturally dilated or there has been leakage of the medication back along the catheter, thereby defeating the purpose of administering the medication.

For some time, it has been recognized that certain drugs in liquid form could improve the relaxation of the cervix even though substantial amounts thereof leaked through the cervix, provided that such leaked amounts could be contained or retained adjacent the external os.

Accordingly, a primary object of this invention is the provision of an improved catheter and method capable of delivering a liquid medication into the extra-amniotic space of an impregnated uterus so that leakage of the medication is virtually eliminated and, to the extent that some leakage occurs, it is essentially trapped adjacent the external os of the cervix where it can continue to perform its function of inducing dilation of the cervix.

A further object of this invention is the provision of a catheter, as aforesaid, having two flanges arranged for location externally of and at the opposite ends of the cervix so as to prevent accidental ejection or ascension of the catheter relative to the uterus.

SUMMARY OF THE INVENTION

The objects and purposes of the invention, including those set forth above, have been met by providing a catheter comprised of a resiliently flexible tube capable of insertion through the birth canal and the cervix into the extra-amniotic space within an impregnated uterus. A pair of spaced flanges are mounted upon the tube and positioned so as to be adjacent to and externally of the opposite ends of the cervix.

A pear-shaped, inflatable balloon member surrounds and is secured to the tube between the flanges for the purpose of engaging and dilating the walls of the cervix. Conduit means is connected to said balloon member to inflate same and conduit means is connected to said tube for delivering a liquid medication through said tube and into said extra-amniotic space.

The terms "upper", "lower" and words of similar import shall have reference to the invention as appearing in FIG. 1. The words "inner", "outer" and derivatives thereof shall have reference to the geometric center of said catheter and parts associated therewith, as well as the uterine cavity and cervix.

Other objects and purposes of this invention will become apparent to persons familiar with this type of equipment upon reading the following description and examining the attached drawings, in which:

FIG. 1 is a side elevational view of a catheter embodying the invention and a central cross-sectional view of a cervix and impregnated uterus in which the catheter is operably located.

FIG. 2 is a sectional view of said catheter taken along the line II—II in FIG. 1.

DETAILED DESCRIPTION

The catheter 10, a preferred embodiment of which is disclosed in FIG. 1, is comprised of a central tube 11 which is resiliently flexible and preferably fabricated from an inert elastomer. The lower end of the tube 11 is preferably integral with a flexible conduit 12 which at its other end is engageable with and connectible to means, such as the syringe 13, for causing a liquid to pass through the conduit and into the tube 11. The upper end of the tube 11 has one or more openings 14 through which said liquid can pass, for example, from the tube 11 into the extra-amniotic space 16 within the uterus 17.

An upper or inner and elongated flange 18 is preferably integral with and penetrated by the tube 11 near the upper end thereof, but below the openings at 14. The lengthwise extent of flange 18 is preferably such that it can be moved through the undilated cervix 20 and into the extra-amniotic space without injuring the cervix. However, the flange 18 must be of sufficient length that its opposite end portions will remain in engagement with the wall of the uterus adjacent the internal os 19 after the desired dilation of the cervix has occurred in order to oppose accidental or unintentional ejection of the catheter during the process of effecting the treatment.

A lower cup-shaped flange 22 encircles and is secured to the tube 11 near the lower end thereof so that it is closely adjacent the external os 23 of the cervix 20 when the upper flange 18 is adjacent the internal os 19. The flange 22, which is resiliently flexible, prevents accidental ascension of the catheter relative to the uterus and also seals the zone around the external os within the birth canal 24 so that any liquid which might seep through the cervix is retained or contained closely adjacent the external os 23.

The flanges 18 and 22 are preferably fabricated from an inert elastomer.

An inflatable balloon member 26, which is preferably made of an inert elastomer, completely encircles the tube 11 between the flanges 18 and 22. The upper and lower ends of the balloon member 26 are secured to and/or integral with the tube 11 so that the balloon member can be inflated.

A flexible conduit 27 extends through and is either secured to or integral with the lower flange 22 adjacent the tube 11. The upper end of said conduit extends into the fluid-tight, annular chamber 28 within the balloon member 26 and surrounding the tube 11.

As shown in the Figures, the balloon member 26, when inflated, has a pear-shaped external contour which closely corresponds to the internal shape of the cervix 20, as defined by the walls thereof, when said cervix is dilated. Accordingly, the balloon member 26 fits snugly within the dilated cervix not only to improve the dilation thereof but to virtually prevent leakage of the fluid back through the cervix, particularly after substantial dilation has been achieved.

The conduit 26 is preferably connected to a constant administration pump 31 or other infusion device whereby a liquid is urged through the conduit into the chamber 28 at a substantially constant and continuous pressure thereby causing the balloon member 26 to be inflated and to assist in the dilation of the cervix.

The parts of the catheter, and particularly the tube 11, balloon member 26 and flanges 18 and 22 are preferably fabricated from an inert plastic such as a diorganopolysiloxane elastomer (or rubber) including room temperature cured silicon rubber and heat cured silicon rubber.

OPERATION

While the operation of the catheter and its associated components will be apparent from the foregoing description thereof, a brief summary of such operation follows.

The catheter 10 is inserted through the birth canal and then into the cervix until the cup-shaped lower flange 22 engages the wall at the inner end of the birth canal adjacent the cervix. When this engagement occurs, the upper flange 18 will be within the amniotic space adjacent the upper end of the cervix. During this insertion of the catheter, the balloon member 26 will be deflated and, accordingly, closely surrounding the tube 11.

The conduit 12 can be attached to a syringe, or other source of medication under pressure, either before or after the insertion of the catheter into the cervix. Also, the pump 31 can be connected to the conduit 27 either before or after said insertion of the catheter. An abortion causing liquid, for example, is now urged by the syringe 13 into the tube 11 and thence through the opening 14 into the extra-amniotic space 16. Thereafter, the pump 31 is energized so that dilation of the cervix is urged by the balloon member 26. Some of the fluid may seep back through the cervix, especially during the initial stages of the abortion process. However, such seeped fluid will be contained by the cupped flange 22 adjacent the external os where its presence, particulary where it is a prostaglandin, will tend to augment dilation of the cervix.

When the abortion process has been completed and appropriate dilation of the cervix has been accomplished, the conduit 27 is disconnected from the pump so that the balloon member 26 can deflate and, thereafter, the catheter 10 can be removed from the cervix and down through the birth canal.

Although a particular preferred embodiment of the invention has been disclosed in detail for illustrative purposes, it will be recognized that variations or modifications of the disclosed method and/or apparatus, including the rearrangement of parts, lie within the scope of the present invention.

The embodiments of the invention in which an exclusive property or privilege is claimed are defined as follows:

1. A device for administering liquid medication to the extra-amniotic space of an impregnated uterus, comprising:
    an elongated, resiliently flexible tube open at opposite ends thereof and of sufficient lenth to extend through the cervix and into said extra-amniotic space of a uterus at one end and into the birth canal at the other end;
    first conduit means connected to the other end of said tube means and extendable through and beyond the birth canal for permitting a liquid medication to be supplied through said tube into said extra-amniotic space;
    first and second flanges secured to said tube and being spaced from each other along said tube by a distance approximately equal to the distance between the uterus and the birth canal at the opposite ends of the cervix;
    said first flange being positionable within the extra-amniotic space of said impregnated uterus directly adjacent the internal os of the cervix for preventing accidental ejection of the tube from the uterus;
    said second flange being cup-shaped and positionable within the birth canal closely adjacent the external os of the cervix for preventing accidental ascension of the tube relative to the uterus, said cup-shaped second flange having a central portion thereof disposed closely adjacent but slightly spaced from the external os to collect any liquid medication which seeps back through the cervix, the cup-shaped second flange having a rim which is snugly engageable with the wall of the birth canal surrounding the external os;
    a resiliently flexible, inflatable, substantially cylindrical member disposed between said flanges and connected to said tube to define a fluid-tight annular chamber surrounding said tube, said member when inflated snugly engaging the wall of the cervix; and
    second conduit means connected to said chamber within said inflatable member and extendable therefrom through and beyond said birth canal for supplying an inflating fluid to said chamber.

2. A device according to claim 1, wherein said first conduit is connected to a source of liquid medication under pressure; and
    wherein said second conduit is connected to a source of fluid including means for maintaining a predetermined pressure upon said fluid.

3. A method for delivering a liquid medication into the extra-amniotic space of an impregnated uterus, comprising the steps of:
    providing an elongated open-ended tube having a first flange thereon adjacent one end thereof and a second cup-shaped flange which opens toward the first flange and is spaced therefrom along said tube by a preselected distance which is slightly greater than the length of the cervix;
    inserting the tube through the birth canal and the cervix so that said one end thereof extends into said extra-amniotic space;
    positioning said tube so that said first flange is disposed within the extra-amniotic space closely adjacent the internal os of the cervix for preventing accidental ejection of the tube and said second flange is disposed closely adjacent but slightly spaced from the external os of the cervix for preventing accidental insertion of the tube;

causing a supply of said medication to flow through said tube and into said extra-amniotic space;

preventing the escape of said medication from said extra-amniotic space into said birth canal by collecting any seepage of medication through the cervix within said cup-shaped second flange; and 4. A method according to claim 3, including the step of positioning said cup-shaped second flange with the rim thereof disposed in snug engagement with the end wall of the birth canal surrounding said external os.

5. A method according to claim 4, including the steps of:

providing an inflatable balloonlike member on said tube in surrounding relationship thereto and disposed between said first and second flanges;

maintaining said balloonlike member in a deflated condition during insertion of said one end of the tube through the cervix into said extra-amniotic space; and inflating said member to cause same to engage and dilate the wall of said cervix after the medication has been supplied through said tube into said extra-amniotic space.

* * * * *

UNITED STATES PATENT AND TRADEMARK OFFICE
CERTIFICATE OF CORRECTION

PATENT NO. : 4 100 923
DATED : July 18, 1978
INVENTOR(S) : Edward M. Southern

It is certified that error appears in the above-identified patent and that said Letters Patent are hereby corrected as shown below:

Column 5, after line 14 (actual line 11); insert

---dilating said cervix.---.

Signed and Sealed this

Sixth Day of March 1979

[SEAL]

Attest:

RUTH C. MASON
Attesting Officer

DONALD W. BANNER
Commissioner of Patents and Trademarks